(12) United States Patent
Walston et al.

(10) Patent No.: US 10,648,977 B2
(45) Date of Patent: May 12, 2020

(54) ANGIOTENSIN RECEPTOR AUTOANTIBODIES AS BIOMARKER FOR EFFECTED USAGE OF ANGIOTENSIN RECEPTOR BLOCKERS

(71) Applicant: THE JOHNS HOPKINS UNIVERSITY, Baltimore, MD (US)

(72) Inventors: Jeremy D. Walston, Baltimore, MD (US); Peter M. Abadir, Woodstock, MD (US); Alka Jain, Columbia, MD (US); Neal Fedarko, Columbia, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/769,617

(22) PCT Filed: Oct. 28, 2016

(86) PCT No.: PCT/US2016/059363
§ 371 (c)(1),
(2) Date: Apr. 19, 2018

(87) PCT Pub. No.: WO2017/075380
PCT Pub. Date: May 4, 2017

(65) Prior Publication Data
US 2018/0306786 A1 Oct. 25, 2018

Related U.S. Application Data

(60) Provisional application No. 62/248,641, filed on Oct. 30, 2015.

(51) Int. Cl.
| | | |
|---|---|---|
| *A61K 31/513* | (2006.01) | |
| *A61K 31/4184* | (2006.01) | |
| *A61K 31/41* | (2006.01) | |
| *A61K 31/4178* | (2006.01) | |
| *G01N 33/564* | (2006.01) | |

(52) U.S. Cl.
CPC ........... *G01N 33/564* (2013.01); *A61K 31/41* (2013.01); *A61K 31/4178* (2013.01); *A61K 31/4184* (2013.01); *A61K 31/513* (2013.01); *G01N 2800/52* (2013.01)

(58) Field of Classification Search
CPC .. G01N 33/564; G01N 2800/52; A61K 31/41; A61K 31/4184; A61K 31/4178; A61K 31/513
See application file for complete search history.

(56) References Cited

U.S. PATENT DOCUMENTS

| | | |
|---|---|---|
| 2010/0098688 A1 | 4/2010 | Schulze-Forster et al. |
| 2015/0238465 A1 | 8/2015 | Abadir et al. |

FOREIGN PATENT DOCUMENTS

| | | |
|---|---|---|
| WO | 2008/015219 A1 | 2/2008 |
| WO | 2014/144095 A2 | 9/2014 |

OTHER PUBLICATIONS

Yang Xia, Rodney E. Kellems, Angiotensin Receptor Agonistic Autoantibodies and Hypertension Preeclampsia and Beyond, Circ Res. Jun. 21, 2013;113(1):78-87 (Year: 2013).*
Michael L.X. Fu, et al., Autoantibodies against the angiotensin receptor (AT1) in patients with hypertension, Journal of Hypertension 2000, 18:945±953 (Year: 2000).*
International Search Report for Application No. PCT/US16/59363 dated Jan. 3, 2017.

* cited by examiner

Primary Examiner — Sarah Pihonak
Assistant Examiner — Jason Deck
(74) Attorney, Agent, or Firm — Tarolli, Sundheim, Covell & Tummino LLP (57) ABSTRACT

The invention described herein provides methods for treating a disease or disorder associated with angiotensin receptor signaling in a patient exhibiting elevated levels of AT1R autoantibodies. The invention also provides methods of identifying a patient suffering from a disease or disorder associated with angiotensin receptor signaling that may benefit from treatment with an angiotensin receptor blocker. Patients with elevated levels of AT1R autoantibodies are identified as candidates that particularly benefit from treatment with an angiotensin receptor blocker.

12 Claims, 4 Drawing Sheets

ANGIOTENSIN RECEPTOR AUTOANTIBODIES AS BIOMARKER FOR EFFECTED USAGE OF ANGIOTENSIN RECEPTOR BLOCKERS

CROSS-REFERENCE TO RELATED APPLICATIONS

This application is the U.S. national phase entry of PCT/US2016/059363, with an international filing date of 28 Oct. 2016, which claims the benefit of U.S. Provisional Application Ser. No. 62/248,641, filed 30 Oct. 2015 which is hereby incorporated by reference in its entirety.

STATEMENT REGARDING FEDERALLY SPONSORED RESEARCH OR DEVELOPMENT

This invention was made with government support under Grant Nos. 1R21AG43284, P30AG021334, 1R01CA149273, awarded by the National Institutes of Health (NIH), and Grant No. W81WH-101-1-0239 awarded by the Department of Defense. The government has certain rights in the invention.

BACKGROUND

In addition to a classic role in homeostatic regulation of blood pressure and fluid balance, components of the Renin Angiotensin System (RAS) have also been implicated in tissue remodeling and wound repair. RAS is present in virtually every organ system and a local and independently regulated RAS in human monocytes has been identified. The binding of Angiotensin II, the main RAS effector hormone, to the angiotensin II type 1 receptor (AT1R) increases the production of the inflammatory molecules and regulates multiple steps in the inflammatory process. Inappropriate activation of the RAS may contribute to chronic inflammation.

The etiologies of aberrant RAS activation are not known. Autoantibodies that react with the AT1R (AT1RaAbs) and increase expression and function of the receptor in an apparent positive feedback loop have been previously identified in pre-eclampsia. AT1RaAbs have also been linked to transplant rejection and malignant hypertension. A pro-inflammatory cascade has been proposed that comprises antibody binding, signal transduction through ERK1/2, an increase in reactive oxygen species, NADPH oxidase expression, and nuclear factor-kappa B (NFκB) activation. Activation of this pro-inflammatory pathway has been suggested as a potential mechanism for endothelial damage observed in persons with hypertension and cardiovascular disease.

Older adults who are particularly vulnerable to a host of adverse health outcomes including falls, functional decline, disability, multimorbidity and early mortality exhibit a frailty phenotype that can be identified using a validated clinical tool. Substantial evidence supports the association of chronic inflammation with this older at-risk population. Levels of IL-6 and neutrophil, monocyte and total white blood cell counts are significantly correlated with aggregate risk in older populations. Contributory factors to sustained inflammatory activation are not well defined, but multiple chronic disease states, redox imbalance, senescent cells, and increased body fat have been suggested.

Angiotensin receptor blockers (ARBs) provide cardiovascular protection, in part, through their vascular and anti-inflammatory effects. However, their efficacy and utility in the presence of AT1RaAb is unknown. There exists a need to investigate the effects of AT1RaAb in the therapeutic usage of ARBs. Likewise, there is a need to develop improved therapeutic methods that can take advantage of a patient's levels of AT1RaAb.

SUMMARY

In certain aspects, the invention provides methods for treating a disease or disorder associated with angiotensin receptor signaling comprising:
a) determining a level of angiotensin receptor autoantibodies in a patient sample;
b) comparing the level of angiotensin receptor autoantibodies in the patient sample to a reference standard; and
c) if the level of angiotensin receptor autoantibodies in the patient sample is higher than the reference standard, then administering to the patient an effective amount of an angiotensin receptor blocker.

In certain aspects, the invention provides methods for identifying a patient suffering from a disease or disorder associated with angiotensin receptor signaling that may benefit from treatment with an angiotensin receptor blocker, comprising determining the level of angiotensin receptor autoantibodies in a patient sample compared to a reference standard, wherein a higher level of angiotensin receptor autoantibodies in the patient sample compared to a reference standard indicates that the patient may benefit from treatment with an angiotensin receptor blocker.

DETAILED DESCRIPTION OF THE INVENTION

Chronic inflammation underlies a number of diseases with high morbidity and mortality. In two distinct groups, higher serum levels of AT1RaAb were strongly associated with deficits in functional measures and an increased at-risk status. The risk of all-cause mortality was almost 4 times higher than in those with lower AT1RaAb levels. This excess risk of death did not diminish after multiple adjustments. ARB treatment appears to be most protective in those older adults with higher serum levels. The relationship between RAS activation and lifespan remains unclear. RAS blockade in some animal studies results in a 25% extension of lifespan as well as improved physical performance. However, in human studies, the response to RAS blockade has varied widely, perhaps due to variability in study designs. It is also possible that variable levels of AT1RaAb may be confounding response to treatment. If the association of AT1RaAb levels with risk status is confirmed, studies of RAS blockers might target individuals with high levels of these autoantibodies.

The correlation between IL-6, BP, and serum AT1RaAb is in agreement with previous research documenting the role of inflammation in the development of hypertension and with a role for AT1RaAb as pro-hypertensive autoantibody. Despite the strong correlation between AT1RaAb and serum IL-6, AT1RaAb did not correlate with IFNγ and was weakly correlated with IL1β and TNFα, suggesting a specific activation pattern for cytokines consistent with a Th2 profile rather than a more generalized cytokinemia. It is interesting to note the increase in serum levels of IFNγ in robust older individuals as compared to at-risk older individuals. Though most of the primary functions described for IFNγ are immune functions, IFNγ also plays a role in muscle repair/function and in fat metabolism and adipocyte gene expression.

Whether the increase in AT1RaAb represents a specific disease-causing agent, or if that increase is a part of age-related global dysregulation of autoantibodies is not clear. Autoantibodies in general are capable of stimulating receptors and causing disease, such as Graves' disease and dilated cardiomyopathy. In our study we observed an association between serum level of AT1RaAb and: cytokines that have been linked to at-risk status (IL-6 and TNFα); functional measures associated with risk status (walking speed and grip strength); and poor outcomes (falls, death). It is not known to what extent AT1RaAb, acts systemically, e.g. via cytokinemia, or more locally, perhaps binding to AT1R on skeletal muscles, neurons and neuromuscular junctions. Variability in serum levels of these autoantibodies may explain some of the variability in results of studies of RAS blockade for improving muscle strength and physical performance in older individuals.

Our data suggests that the use of ARBs attenuated the effects of AT1RaAb on grip strength. Although hints of this effect may be gleaned from previous reports documenting protective effects for ARBs in older hypertensive persons, our data suggests that this effect may be partially explained by the presence of AT1RaAb in these older adults. The increased incidence of falls and serious injuries with the use of ARBs has been previously reported. Interestingly this effect was striking in the low AT1RaAb group, but was attenuated in the high AT1RaAb. This finding suggests that ARBs may be safer and more effective in persons with a dysregulated RAS (e.g. AT1RaAb mediated).

In the light of the present study and reports on the effects of AT1RaAb on cytokines, reactive oxygen species and endothelial dysfunction, elevated serum levels of AT1RaAb may have contributed to the precipitation and progression of physical decline in those older individuals at risk for negative health outcomes (increased falls and mortality). More studies are required to fine tune the utilization of AT1RaAb as a screening tool and for selection of individuals that might benefit most from RAS blockade. Additionally, the association of risk status with serum levels of AT1RaAb provides a plausible biological pathway for RAS-mediated chronic inflammation and subsequent disease progression that can be probed for therapeutic intervention.

Accordingly, in certain embodiments, the invention provides a method or treating a disease or disorder associated with angiotensin receptor signaling, the method comprising:
a) determining a level of angiotensin receptor autoantibodies in a patient sample;
b) comparing the level of angiotensin receptor autoantibodies in the patient sample to a reference standard; and
c) if the level of angiotensin receptor autoantibodies in the patient sample is higher than the reference standard, then administering to the patient an effective amount of an angiotensin receptor blocker.

In other aspects, the invention provides a method of identifying a patient suffering from a disease or disorder associated with angiotensin receptor signaling that may benefit from treatment with an angiotensin receptor blocker, comprising determining the level of angiotensin receptor autoantibodies in a patient sample compared to a reference standard, wherein a higher level of angiotensin receptor autoantibodies in the patient sample compared to a reference standard indicates that the patient may benefit from treatment with an angiotensin receptor blocker.

In certain embodiments, the reference standard is determined experimentally, as indicated in Example 1.

In certain embodiments, the reference standard is between about 5 µg/mL to about 10 µg/mL, between about 6 µg/mL to about 9 µg/mL, between about 7 µg/mL to about 9 µg/mL, between about 7.5 µg/mL to about 8.5 µg/mL, about 8 µg/mL, or about 8.2 µg/mL.

In certain preferred embodiments, the reference standard is about 8.2 µg/mL.

In certain embodiments, the disease or disorder is associated with aberrant angiotensin type 1 receptor ($AT_1R$) signaling.

In certain embodiments, the disease or disorder is typically treated with an angiotensin receptor blocker.

In certain embodiments, the disease or disorder is an inflammatory disorder.

In certain embodiments, the disease or disorder is chronic inflammation.

In certain embodiments, the disease or disorder is a wound healing disorder.

In certain embodiments, the disease or disorder is diabetes, atherosclerosis, obesity, hypertension, diabetic nephropathy, congestive heart failure, or cancer.

In certain embodiments, the patient sample is a blood sample.

In certain embodiments, the patient sample is a blood plasma sample.

In certain embodiments, the angiotensin receptor blocker is losartan, irbesartan, olmesartan, candesartan, valsartan, fimasartan, or telmisartan, or a pharmaceutically acceptable salt thereof.

In certain embodiments of the invention, if the level of angiotensin receptor autoantibodies in the patient sample is lower than the reference standard, then an angiotensin receptor blocker is not administered to the patient.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, the aqueous solution is pyrogen-free, or substantially pyrogen-free. The excipients can be chosen, for example, to effect delayed release of an agent or to selectively target one or more cells, tissues or organs. The composition is suitable for topical administration, and can also be present in a transdermal delivery system, e.g., a skin patch, or in an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, absorption through the oral mucosa (e.g., sublingually); anally, rectally or vaginally (for example, as a pessary, cream or foam); transdermally (for example as a patch applied to the skin); and topically (for example, as a cream, ointment or spray applied to the skin, or as an eye drop). In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, and then, if necessary, shaping the product.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical administration include powders, sprays, ointments, pastes, creams, lotions, gels, hydrogels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In another aspect, the invention provides pharmaceutical compositions of the compounds described herein, optionally in admixture with one or more pharmaceutically acceptable excipients. Preferably, the compositions are suitable for topical administration.

In yet another aspect, the invention provides methods for administering the compounds and compositions described herein, e.g., for the treatment of an inflammatory disorder or a cutaneous wound in a subject in need thereof.

Compounds of any of the structures described herein and any composition of these compounds may be used in the manufacture of medicaments for the treatment of any diseases or conditions disclosed herein.

Methods of Treatment

Chronic wounds are among the most common, painful, debilitating and costly conditions in diabetics and in older adults, and are an important portal for bacterial infections that often lead to amputations, sepsis and mortality. In diabetic and aging skin, chronic inflammation commonly accompanies poor wound healing and increases the risk for chronic non healing wounds. In diabetic and aged skin, the angiotensin system is dysregulated with aberrant angiotensin AT1 receptors (AT1R) signaling that increases inflammatory burden leading to thinning of epidermis, degeneration of collagen, fracture of dermal layer, and atrophy of subcutaneous fat. The reason for the activation of the angiotensin receptors is not known, but stimulatory AT1R autoantibodies (AT1RaAb) increase AT1R signaling, and likely thereby impair wound healing by irreversibly activating AT1R. We have developed a topical Angiotensin Receptor blocker treatment that effectively treats chronic wounds in preclinical studies, but the effects of this topical treatment with angiotensin receptor blockers (ARBs) in older individuals may depend on levels of AT1RaAb since AT1RaAb may compete with ARBs for receptor occupancy. Our technology is aimed at specifically determining the levels of these autoantibodies in older and diabetic patients with chronic wounds. We will utilize the level of the antibody as a serum biomarker to identify a subset group of patients with elevated AT1RaAb associated with chronically delayed wound healing that will likely respond to topical treatment with angiotensin receptor blockers.

The invention also provides methods of treating a cutaneous wound, comprising administering to the cutaneous wound in a subject in need thereof a therapeutically effective amount of an angiotensin receptor blocker, wherein the subject exhibits levels of AT1RaAb that are higher than a reference standard, as is described herein.

In certain embodiments, the cutaneous wound is a chronic wound.

In certain embodiments, the cutaneous wound is a diabetic skin ulcer.

In certain embodiments, the cutaneous wound is an ulcer associated with aging skin.

In certain embodiments, the wound is a burn, an electrical injury, a radiation injury, a sunburn, a gun shot injury, an explosives injury, a post-surgical wound, a keloid, scar tissue, psoriasis, a superficial dermatologic resurfacing, or a skin lesion due to an inflammatory condition.

In certain embodiments, the cutaneous wound is in a tissue associated with an upregulation in angiotensin II type 1 receptors.

Administration of the angiotensin receptor blocker can be topical. Alternatively, administration is buccal administration.

In certain embodiments, the pharmaceutical composition is administered at least 3 days, at least 4 days, at least 5 days, or at least 6 days after wounding. For example, the angiotensin receptor blocker composition may be administered to a patient after the inflammatory phase of wound healing has passed. The angiotensin receptor blocker composition may be administered to the patient in the proliferative/remodeling phase of wound healing.

In certain embodiments, the subject is a mammal, for example, a human.

Definitions

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

EXAMPLES

Materials and Methods
Case Control Study Design and Participants.

Eighty-seven, community dwelling older adults, age 70-90 years, and 39 adults aged 20-30 years living in the Baltimore, Md. area were recruited with the goal of developing a discovery set stratified into case (older at-risk) and controls (young and older robust) groups. Exclusion criteria included angiotensin receptor blockers, angiotensin converting enzymes inhibitors, estrogen replacement therapy, corticosteroids, methotrexate, and non-steroidal anti-inflammatory drugs (NSAID) or other immune modulating agents. A uniform structured clinical evaluation was performed on each participant. At-risk status was assessed using a commonly utilized and well-validated frailty phenotype screening tool that consists of grip strength and walking speed measurements, as well as weight loss, fatigue, and physical activity questions. To replicate our findings in the Baltimore participants and study the effects of chronic treatment with angiotensin receptor blockers, samples from a second patient population, age 70-90 years were obtained from the Religious Orders Study and the Rush Memory and Aging Project, longitudinal clinical-pathologic studies of chronic conditions of old age. Participants were recruited from >40 residential facilities across the metropolitan Chicago area, including subsidized senior housing facilities, retirement communities, and retirement homes, in addition to social service agencies and Church groups.

The number of cases and controls needed from the Chicago group were determined by performing a sample size calculation using the observed mean functional measures (walking speed and grip strength) above and below the optimal AT1RaAb cut off value in the Baltimore population, the standard deviation of those measures, and an 80% power to detect the relevant difference between means at a significance of 0.05. For grip strength, a mean difference of 11 kg, an observed standard deviation of 12, yielded a sample size of 20. For walking speed, a mean difference of 0.31 m/s, a standard deviation of 41, yielded a sample size of 30. The larger sample size was used. Cases from the Chicago population were subjects treated with ARBs and matched by age, gender, ethnicity, BMI and blood pressure to controls (subjects who were not treated with ARBs). Data collected on subjects from both populations included measures of demographics (age, gender, ethnicity), physiology (BMI, blood pressure, comorbid conditions, medications), function (grip strength and walking speed), and outcome (falls and mortality). Study subjects were enrolled under informed consent and the study protocol had local Institutional Review Board approval.

Procedures.

Blood was drawn and processed for serum isolation following standard clinical procedures. A quantitative antigen-down capture ELISA was developed in-house to measure AT1RaAb in serum samples. Briefly, purified capture antigen, AFHYESQ, was coated at 40 ng/well. Wells were blocked with Neptune blocking reagent (ImmunoChemistry Technologies, Bloomington, Minn., USA). Serum from subjects was diluted 1:200, serum and antibody dilutions were made in Tris buffered saline containing 0.05% Tween 20 and 10% Neptune blocking reagent. Each subject had duplicate aliquots on coated and uncoated wells, thus the assay measures both specific and non-specific binding for each subject. Additionally 16 wells (half coated with antigen and half uncoated) were reacted with 1:3 serial dilutions starting at 10 µg/ml of an affinity purified, goat anti-rabbit anti-AFHYESQ IgG antibody to generate a standard curve. A 1:2,000 dilution of a secondary goat anti-human IgG detection antibody conjugated to HRP was used in conjunction with 3,3',5,5'-tetramethylbezidine substrate (Kirkegaard & Perry Laboratories, Gaithersburg, Md., USA). Serum interferon-γ (IFNγ), interleukin-1β (IL1β), interleukin-6 (IL-6) and tumor necrosis factor-α (TNFα) were assayed using a multiplexed sandwich ELISA (Mesoscale Diagnostics, Rockville, Md., USA) following the manufacturer's protocol.

Statistical Analysis.

Nonparametric analyses were used because the distribution of serum levels of AT1RaAb failed the D'Agostino & Pearson omnibus normality test. Comparisons of AT1RaAb values between groups (at-risk status) were by Mann-Whitney U-test. Receiver operating characteristic (ROC) curve analysis was used for predicting at-risk status and identifying the optimal cut off value of AT1RaAb. Pairwise correlations between AT1RaAb and clinical correlates or functional outcomes were assessed using Spearman rank correlations. Age adjusted and multiple-adjusted random effects models were used to compare the grip strength between AT1RaAb groups. A logistic regression model for baseline falls was constructed to characterize the independent association of AT1RaAb and ARB treatment groups with falls. To evaluate the relationship between AT1RaAb and ARBs groups with mortality, Kaplan-Meier survival analyses and Cox proportional hazards regression model were performed.

Example 1. Risk Status, Pro-Inflammatory Cytokines, and $AT_1R_{aAb}$ Levels

Figure 1:
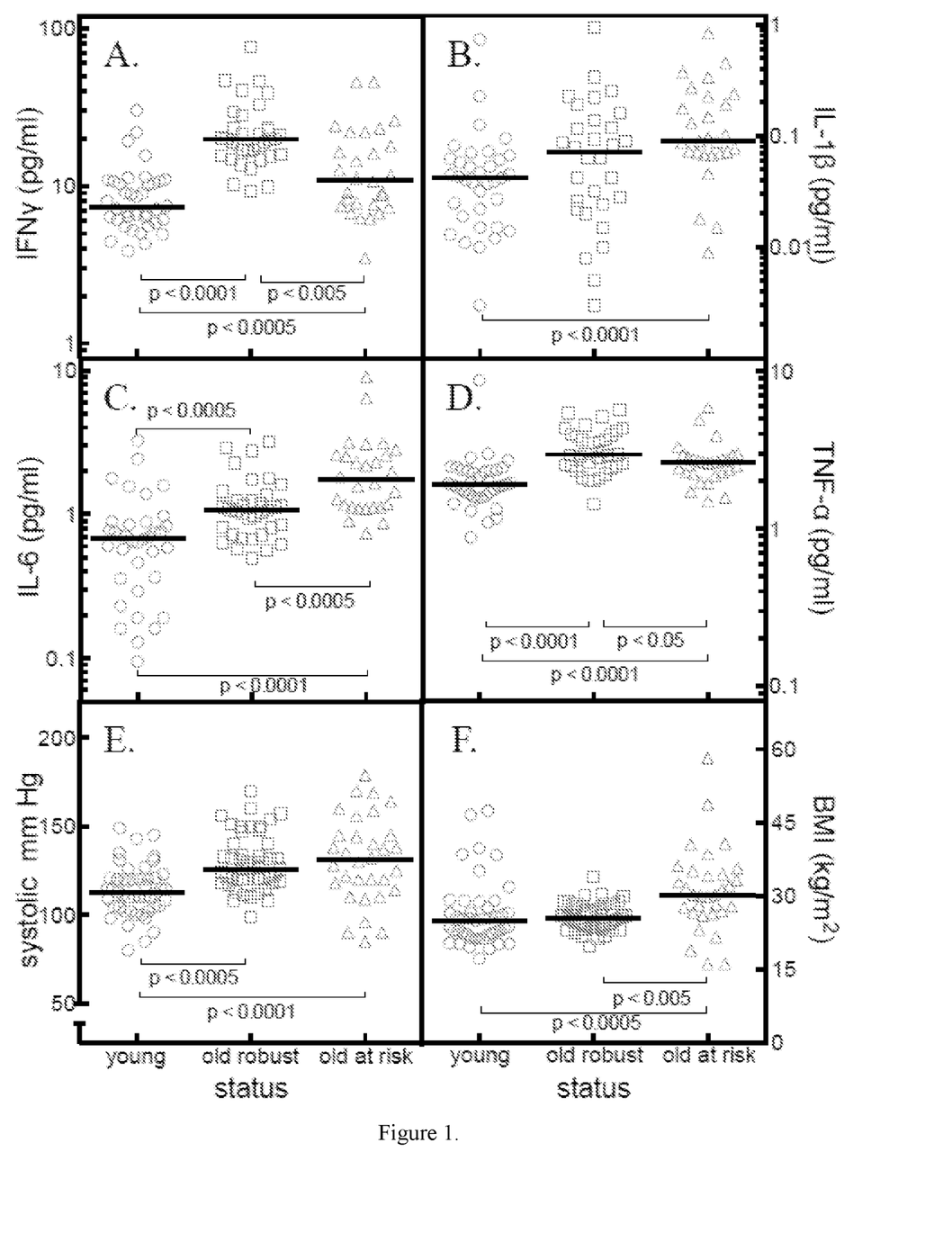
FIG. 1 consists of Panels A-F and depicts physiologic measures in the Baltimore population. Serum levels of (Panel A) IL-6, (Panel B) TNFα, (Panel C) IFNγ, (Panel D) IL-1β, and BP and BMI (Panels E and F) measures in participants were segregated by age and at risk status. Data points represent mean values of duplicate measures for cytokines in individual persons; young (○), older robust (□), and older at-risk (Δ). Bar represents median value. Groups were compared by Mann Whitney U-test.

Demographic and clinical variables of the primary and secondary populations are presented in Table 1. The primary study population was further segregated using the Fried frailty criteria to distinguish between robust and at-risk individuals. Significant differences between young, old robust, and old at-risk groups were observed in the distribution of four pro-inflammatory cytokines (FIG. 1, panels A-D). At-risk individuals had higher levels of serum IL-6 with a median value of 1.7 (range 0.7-0.0) pg/ml versus 1.1 (range 0.5-3.0) pg/ml for old robust subjects, p<0.0005, but lower serum IFNγ in the at-risk as compared to age matched robust controls, 11 (range 3.5-46) pg/ml versus 20 (range 9.3-77) pg/ml, p<0.005. No significant differences were found for IL-1β between old robust and at-risk individuals. Older at-risk individuals also had higher systolic BP and BMI (FIG. 1, panels E and F).

Figure 2:
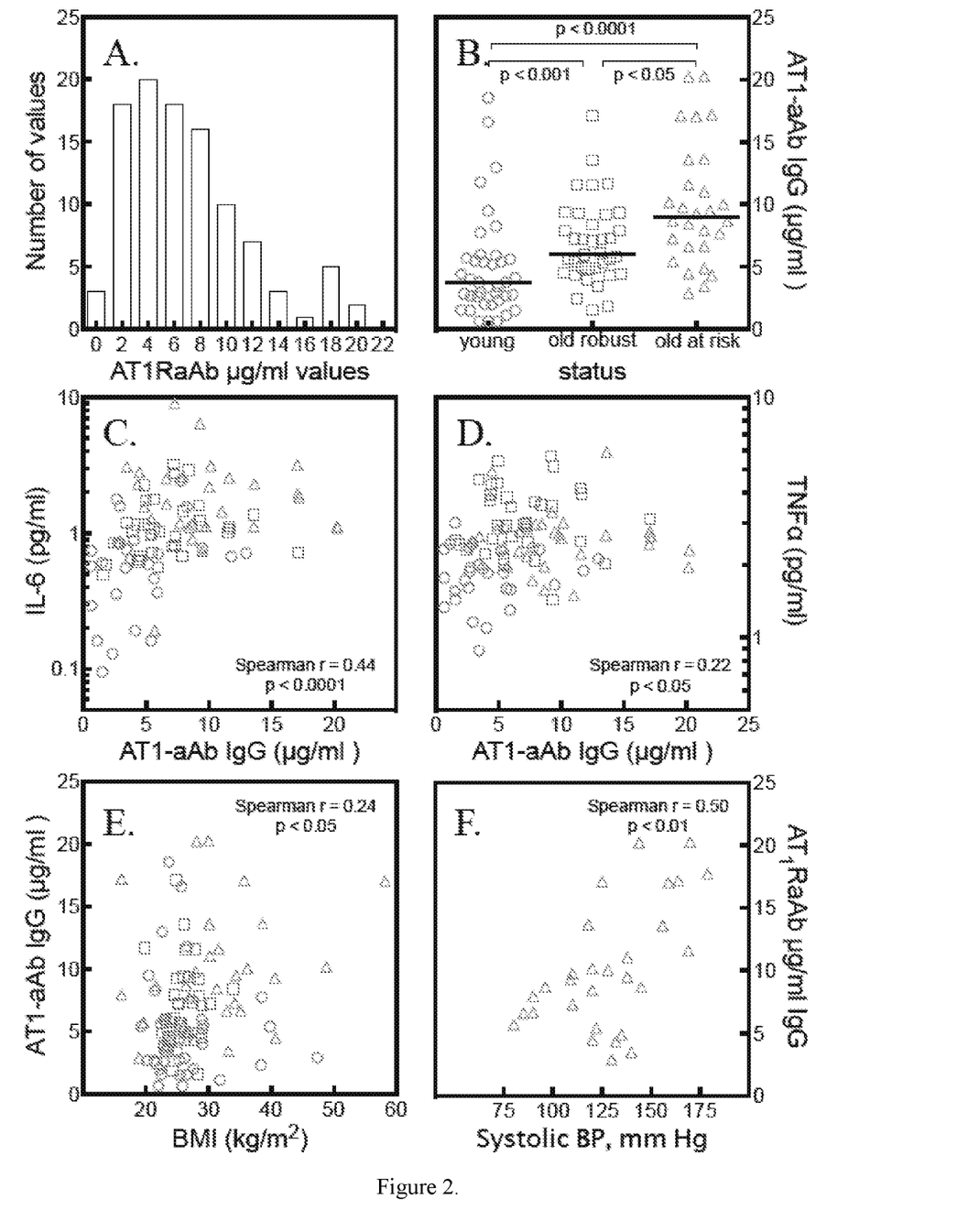
FIG. 2 consists of Panels A-F and depicts characterization and association of serum levels of AT1RaAb with at-risk status, IL-6 and TNFα, BMI and higher BP in the Baltimore population. (Panel A) The distribution of serum levels of AT1RaAb by histogram. (Panel B) Serum levels of AT1RaAb in participants were segregated by group (young, older robust, older at-risk) and compared by Mann Whitney U-test. AT1RaAb levels were segregated by group and plotted as a function of (Panel C) IL-6 and (Panel D) TNFα, (Panel E) BMI and (Panel F) systolic BP. Data points represent individual persons; young (○), older robust, (□) older at-risk (Δ). Bar is median of the group. The pair-wise association between AT1RaAb and age, IL-6, TNFα, BP and BMI were analyzed by Spearman correlation.

To measure serum levels of AT1RaAb in our study participants, we developed a quantitative antigen-down capture ELISA. Serum levels of AT1RaAb exhibited a skewed distribution (FIG. 2, panel A). When persons older than 70 years of age were segregated by risk status, at-risk individuals had higher median levels, 9.0 (range 2.8-20.3) µg/ml, of serum AT1RaAb as compared to either the young or robust older individuals, 3.7 (range 0.6-18.5) µg/ml and 6.0 (range 1.6-17) µg/ml, respectively (FIG. 2, panel B). ROC curve analysis for detecting at-risk status yielded an area under the curve of 0.76±0.05 and, at a cut-off value of 8.2 µg/ml, a specificity of 80% (95% CI 69-88) and sensitivity of 61% (95% CI 41-78). Based on the ROC curve analysis, on average the at-risk individuals will be correctly classified as such 76% of the time based on the AT1RaAb cutoff. Logistic regression analysis revealed that individuals with AT1RaAb levels above 8.2 µg/ml were 3.9 (95% CI 1.38-11.0) times more likely to be at risk after correcting for age (p<0.05). When analyzed in pre-specified age groups, individuals aged 70-75, with AT1RaAb≥8.2 were 4.88 (95% CI 1.50-18.86) times more likely to be at risk (p<0.01) compared with those with AT1RaAb<8.2 µg/ml. Among individuals who are older than 75 years of age, those with AT1RaAb≥8.2 µg/ml were 9.0 (95% CI 1.3-63.8) times more likely to be at risk compared with those with AT1RaAb<8.2 µg/ml (p<0.05).

The independent association of risk status with pro-inflammatory markers and with AT1RaAb levels, suggested that serum levels of AT1RaAb may correlate with levels of cytokines previously described as markers of at-risk status. There was a strong positive correlation between AT1RaAb and IL-6 (Spearman r=0.44, p<0.0001) and TNFα (Spearman r=0.22, p<0.05) (FIGS. 2 C & D); and the correlations were independent of age or at-risk status. Higher serum levels of AT1RaAb were associated with BMI (Spearman r=0.24, p<0.05), but with higher systolic BP only in the at-risk group (Spearman r=0.50, p<0.01, FIG. 2, panels E & F).

Example 2. $AT_1R_{aAb}$ Levels and Functional Measures

Figure 3:
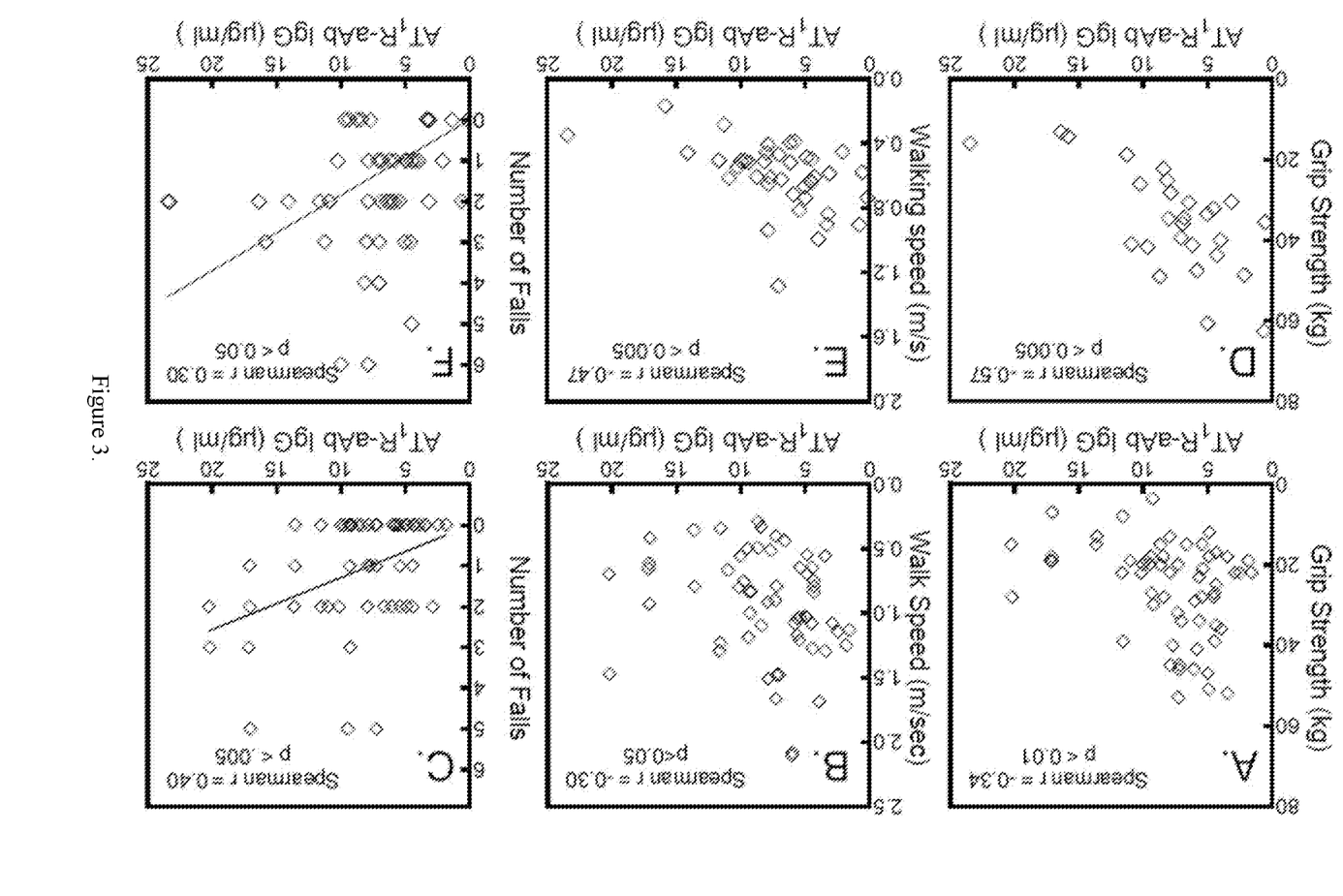
FIG. 3 consists of Panels A-F and depicts AT1RaAb level association with grip strength, walking speed and number of falls, in the Baltimore (Panels A, B and C) and Chicago (Panels D, E and F) populations. Participant's grip strength (Panels A and D), walking speed (Panels B and E) and number of falls (Panels C and F) in older persons were plotted as a function of AT1RaAb. Data points represent individual older persons (◊); bar is median of the group. The association of functional outcomes with AT1-aAbs was assessed by Spearman correlation.

At-risk status has been strongly associated with weaker grip strength and decline in walking speed as well as increased falls and mortality. The association between AT1RaAb levels and functional measures and outcomes was investigated in old robust and old at-risk individuals from the primary population in Baltimore (FIG. 3, panels A-C). The level of AT1RaAbs correlated negatively with grip strength (Spearman r=−0.34, p<0.01), walking speed (Spearman r=−0.30, p<0.05), and positively with number of falls in older individuals (Spearman r=0.40, p<0.005). The mean walking speed was 0.76±0.33 for subjects with A1RaAb levels >8.2 and 1.07±0.40 for subjects with lower A1RaAb levels. The mean grip strength was 19±7.7 for subjects with A1RaAb levels >8.2 and 30±12 for subjects with lower A1RaAb levels.

For the Chicago group, 60 subjects, half treated with ARBs, had their demographic and physiologic covariates, physical function tests, health outcomes, and AT1RaAb levels measured. The Chicago group had a higher average age, proportion of females, number of comorbidities, and reduced grip strength and walking speed compared with the Baltimore group (Table 1). Similar associations between serum AT1RaAb levels and grip strength (Spearman r=−0.57, p<0.005), walking speed (Spearman r=−0.47, p<0.005) and falls (Spearman r=0.30, p<0.05) were observed (FIG. 3, panels D, E). The mean difference between high and low AT1RaAb subject grip strength in the Chicago group was 12 (95% CI 2.6-22), no different from the Baltimore group whose mean difference was 11 (95% CI 5.4-17).

Figure 4:
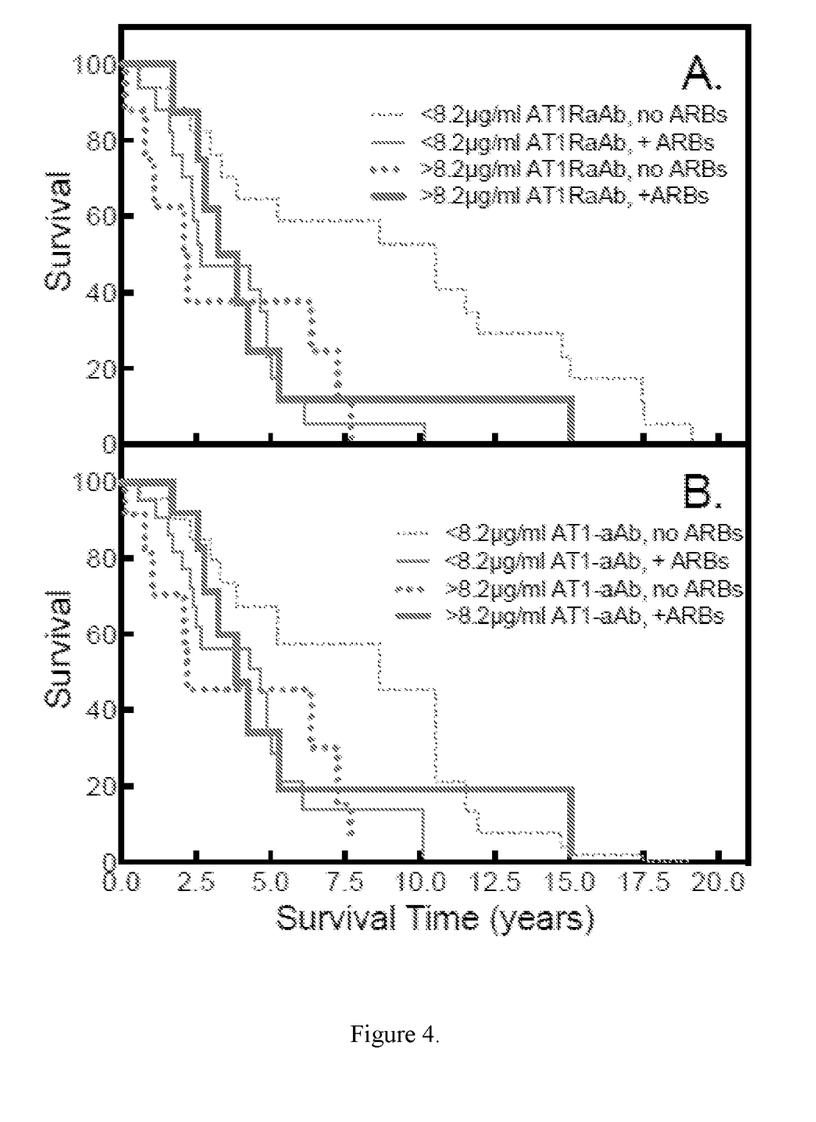
FIG. 4 consists of Panels A and B and depicts mortality associations with AT1RaAb level (Panel A) Unadjusted, and (Panel B) age adjusted survival curves of participants from the secondary population stratified by AT1RaAb levels and ARB use were determined.

The observation of an association between generalized weakness (slower walking speed and weaker grip strength) and higher AT1RaAb levels in the Baltimore group, led to an investigation of the impact of AT1RaAbs on risk for falls and mortality. Logistic regression modeling of AT1RaAb and falls revealed that individuals with serum AT1RaAb≥8.2 µg/ml were 8.5 (95% CI 1.8-39.1) times more likely to fall than those with AT1RaAb<8.2 µg/ml (p=0.006) after adjusting for age and gender. This effect was attenuated and became insignificant, after adjusting for BMI, IL-6 level and number of comorbidities (Table 2—No ARBs users). Cox proportional hazards regression modeling indicated that individuals with AT1RaAb≥8.2 µg/ml were 4.2 (95% CI 1.51-11.68) times more likely to die (mean survival 3.4 years) than those with AT1RaAb≤8.2 µg/ml (mean survival 9.2 years) (p<0.01) after adjusting for baseline age and gender. This relationship remained significant after multiple adjustments (Table 2 and FIG. 4—No ARBs users).

Example 3. Treatment with Angiotensin Receptor Blockers (ARBs)

The effects of ARBs in older individuals may depend on levels of AT1RaAbs since ARBs may compete with AT1RaAbs for receptor occupancy. Multiple-adjusted models were used to assess the effect of ARB treatment on grip strength. Among older individuals not receiving ARBs, there was an average 2.6 (95% CI 0.52-4.68) kg decrease in grip strength for every 1 µg/ml increase in AT1RaAb level after controlling for age. Multiple adjustments including gender, comorbidities, BMI and IL-6, in addition to age did not affect the association in the non-ARB group—a decrease of 2.8 kg (95% CI 0.67-4.93) for every 1 µg/ml increase in AT1RaAb, p<0.01. This relationship was significantly weaker in older individuals receiving ARB treatment after age adjustment where a decrease of 0.01 (95% CI 0.002-0.018) kg for every 1 µg/ml increase in AT1RaAb, p<0.05). Multiple adjustments did slightly increase the positive association in individuals receiving chronic ARB treatment—an increase of 0.03 kg (95% CI 0.005-0.055) in grip strength for every 1 µg/m increase in AT1RaAb, p<0.05. These data suggest that ARB treatment attenuated the negative effects of AT1RaAb on grip strength.

The above observation that ARB use modulated the association between AT1RaAb and grip strength led to logistic regression modeling of the relationship between falls, autoantibodies and ARB treatment (Table 2). In the absence of ARB treatment, AT1RaAb levels were strongly associated with falls, Odds ratio=8.5 (95% CI 1.8-39.1), p=0.006. Thus, a protective effect for ARBs against falls was expected. However, the results indicated that the effect of ARB treatment on fall incidence was linked to the serum levels of AT1RaAb. Among individuals with AT1RaAb≤8.2 µg/ml, those on ARB treatment were 14.2 [95% CI 2.2-90.4] times more likely to fall than those not on ARB treatment (p<0.005). This association between falls and ARB use persisted after multiple adjustments for age, gender, BMI, IL-6 and comorbidities. In individuals with high AT1RaAb (≥8.2 µg/ml), the association between falls and ARB use was attenuated and became insignificant after controlling for gender, comorbidities, BMI and IL-6, in addition to age.

Analysis of ARB effects on mortality showed that in individuals with AT1RaAb levels ≤8.2, a higher mortality was observed in those on ARB treatment (Hazard ratio 2.5 (95% CI 1.09-5.73), p<0.05). This association was not significant after controlling for age, gender, comorbidities, BMI and IL-6. The effect of high levels of AT1RaAb on mortality was attenuated and became insignificant in ARB users, after adjusting for BMI, comorbid conditions and IL-6 levels (Table 2). These observations were unlikely to be caused by demographic or clinical differences between those on ARBs and not on ARBs as the characteristics of Chicago group segregated by ARBs treatment revealed no significant differences except for thyroid disease (Table 3).

TABLE 1

Basic characteristics, main predictors and outcomes of primary (Baltimore) and secondary (Chicago) populations.

| Model Covariates | Primary population (Baltimore) | | Secondary Population (Chicago) (N = 60) |
|---|---|---|---|
| | Young (N = 46) | Old (N = 87) | |
| Age at visit, years (mean ± SD) | 26.0 ± 6.3 | 75.4 ± 13.0 | 84.3 ± 6.6 |
| Female (%) | 31 (67·4%) | 44 (65·7) | 50 (83·3) |
| Systolic blood pressure, mmHg (mean ± SD) | 113 (14) | 131 (24) | 129 (20) |
| Diastolic blood pressure, mmHg (mean ± SD) | 73 (11) | 71 (11) | 73 (11) |
| Total number of comorbidities (%) | 0 | 0.8 ± 0.9 | 1.3 ± 1.3 |
| Log IL-6, (mean ± SD) | −0·5 ± 0·8 | 0.3 ± 0·6 | 0·4 ± 1·0 |
| BMI | 26·3 ± 6·8 | 28·0 ± 6·8 | 25·5 ± 4·4 |
| Main predictors | | | |
| AT1RaAb (median, range) | 3·7 (0·6-18·5) | 7·3 (1·5-20·3) | 6·9 (0·15-55·8) |
| ARBs (%) | 0 | 0 | 30 (50%) |
| Outcomes | | | |
| Grip Strength, kg (mean ± SD) | NA | 26 ± 12 | 16 ± 5.7 |
| Fall (%) | NA | 28 (41·7) | 16 (26·7) |
| Walking speed, m/s (mean ± SD) | NA | 1·0 (0·40) | 0·61 (0·21) |

TABLE 2

Association between AT1RaAb, falls and mortality and the impact of angiotensin receptor blockers in secondary population.

| | AT1RaAb <8.2 µg/ml | | AT1RaAb ≥8.2 µg/ml | |
|---|---|---|---|---|
| | No ARBs | ARBs | No ARBs | ARBs |
| Falls | OR[a] (p value) | OR (p value) | OR (p value) | OR (p value) |
| Un-adjusted | 1·0 (referent) | 14·67 (CI: 2·5-86·2) (p = 0·003) | 8·0 (1·1-60·7) (0·044) | 13·33 (1·7-103·1) (0·013) |
| Age and gender adjusted | 1·0 (referent) | 14·2 (2·2-90·4) (0·005) | 8·5 (1·8-39·1) (0·006) | 11·9 (1·4-99·4) (0·022) |
| Multiple-adjusted[b] | 1·0 (referent) | 30·1 (1·6-556·6) (0·022) | 7·5 (0·5-124·2) (0·16) | 2·8 (0·1-69·1) (0·54) |
| Mortality | HR[c] (p value) | HR (p value) | HR (p value) | HR (p value) |
| Un-adjusted | 1·0 (referent) | 3·92 (1·74-8.81) (0·001) | 3·95 (1·51-10·30) (0·005) | 2·55 (1·03-6·30) (0·042) |
| Age and gender Adjusted | 1·0 (referent) | 2·5 (1·09-5·73) (0·03) | 4·2 (1·51-11·68) (0·006) | 1·89 (0·76-4·68) (0·17) |
| Multiple-adjusted[b] | 1·0 (referent) | 2·56 (0·96-6.83) (0·06) | 4·5 (1·54-13·15) (0·006) | 2·01 (0·73-5·56) (0·18) |

[a]Odds ratio.
[b]Adjusted for age, gender, BMI, log IL-6, and number of comorbidities.
[c]Hazards ratio.

TABLE 3

Characteristics of secondary population segregated by ARB use.

| | No ARB (n = 30) | ARB (n = 30) | p-value |
|---|---|---|---|
| Age, mean (std) | 82·9 (8·4) | 85·7 (4·0) | 0·10 |
| Gender, Male (%) | 22 (84·6%) | 18 (72%) | 0·32 |
| BMI, kg/m² mean (std) | 24.9 (4.4) | 26.2 (4.5) | 0.32 |
| Walking speed, m/s mean (std) | 0·64 (0·24) | 0·59 (0·17) | 0·44 |
| Grip Strength, kg mean (std) | 15·2 (6·8) | 16·4 (4·9) | 0·61 |
| Diabetes (%) | 3 (10%) | 6 (20%) | 0·47 |
| Thyroid (%) | 5 (16·7%) | 12 (40%) | 0·045 |
| Heart Disease (%) | 7 (23·3%) | 7 (23·3%) | 1·0 |
| Stroke (%) | 6 (20%) | 8 (26·7%) | 0·54 |

TABLE 3-continued

Characteristics of secondary population segregated by ARB use.

|  | No ARB (n = 30) | ARB (n = 30) | p-value |
|---|---|---|---|
| Claudication (%) | 5 (16.7%) | 7 (23.3%) | 0.52 |
| Kidney disease (%) | 4 (13.3%) | 9 (30%) | 0.21 |
| LogIL-6, mean (std) | 0.14 (0.74) | 0.59 (1.24) | 0.12 |
| AT1RaAb, µg/ml IgG |  |  |  |
| Mean (std) | 9.8 (10.7) | 8.1 (8.8) |  |
| Median (range) | 6.8 (0.2-56) | 7.0 (0.6-45) |  |
| # of disease, mean (std) | 1.0 (1.1) | 1.6 (1.5) | 0.063 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method for treating a disease or disorder associated with angiotensin receptor signaling, the method comprising:
   a) determining a level of angiotensin receptor autoantibodies in a patient sample;
   b) comparing the level of angiotensin receptor autoantibodies in the patient sample to a reference standard comprising between about 5 µg/mL to about 10 µg/mL angiotensin receptor autoantibodies; and
   c) if the level of angiotensin receptor autoantibodies present in the patient sample is higher than the reference standard, then administering to the patient an effective amount of an angiotensin receptor blocker.

2. The method of claim 1, wherein the level of angiotensin receptor autoantibodies present in the reference standard is selected from the group consisting of: between about 6 µg/mL to about 9 µg/mL, between about 7 µg/mL to about 9 µg/mL, between about 7.5 µg/mL to about 8.5 µg/mL, about 8 µg/mL, and about 8.2 µg/mL.

3. The method of claim 2, wherein the reference standard is about 8.2 µg/mL.

4. The method of claim 1, wherein the disease or disorder is associated with aberrant angiotensin type 1 receptor (AT 1R) signaling.

5. The method of claim 1, wherein the disease or disorder is typically treated with an angiotensin receptor blocker.

6. The method of claim 1, wherein the disease or disorder is an inflammatory disorder.

7. The method of claim 1, wherein the disease or disorder is chronic inflammation.

8. The method of claim 1, wherein the disease or disorder is a wound healing disorder.

9. The method of claim 1, wherein the disease or disorder is diabetes, atherosclerosis, obesity, hypertension, diabetic nephropathy, congestive heart failure, or cancer.

10. The method of claim 1, wherein the patient sample is a blood sample.

11. The method of claim 1, wherein the patient sample is a blood plasma sample.

12. The method of claim 1, wherein the angiotensin receptor blocker is losartan, irbesartan, olmesartan, candesartan, valsartan, fimasartan, or telmisartan, or a pharmaceutically acceptable salt thereof.

* * * * *

UNITED STATES PATENT AND TRADEMARK OFFICE
CERTIFICATE OF CORRECTION

PATENT NO. : 10,648,977 B2
APPLICATION NO. : 15/769617
DATED : May 12, 2020
INVENTOR(S) : Walston et al.

Page 1 of 1

It is certified that error appears in the above-identified patent and that said Letters Patent is hereby corrected as shown below:

In the Specification

Column 1, Lines 15-23, Statement Regarding Federally Sponsored Research or Development, please replace Paragraph with the following:
--STATEMENT REGARDING FEDERALLY SPONSORED RESEARCH OR DEVELOPMENT
This invention was made with government support under AG021334 and CA149273, awarded by the National Institutes of Health and W81XWH-10-1-0239, awarded by the Army Medical Research and Material Command. The government has certain rights in the invention.--

Signed and Sealed this
Ninth Day of June, 2020

Andrei Iancu
*Director of the United States Patent and Trademark Office*